(12) United States Patent
Thramann

(10) Patent No.: US 7,771,473 B2
(45) Date of Patent: Aug. 10, 2010

(54) EXPANDABLE SPINAL FUSION CAGE

(75) Inventor: Jeffery Thramann, Longmont, CO (US)

(73) Assignee: Lanx, Inc., Broomfield, CO (US)

( * ) Notice: Subject to any disclaimer, the term of this patent is extended or adjusted under 35 U.S.C. 154(b) by 1057 days.

(21) Appl. No.: 11/456,038

(22) Filed: Jul. 6, 2006

(65) Prior Publication Data
US 2008/0021558 A1  Jan. 24, 2008

(51) Int. Cl.
*A61F 2/44* (2006.01)
(52) U.S. Cl. .................................. 623/17.11
(58) Field of Classification Search ............ 606/90, 606/99; 623/17.11–17.16
See application file for complete search history.

(56) References Cited

U.S. PATENT DOCUMENTS

| | | | |
|---|---|---|---|
| 5,522,899 A | 6/1996 | Michelson | |
| 5,693,100 A | 12/1997 | Pisharodi | |
| 5,749,916 A | 5/1998 | Richelson | |
| 5,766,199 A | 6/1998 | Heisler | |
| 5,800,438 A * | 9/1998 | Tuke et al. .................. | 606/90 |
| 5,976,187 A | 11/1999 | Michelson | |
| 6,159,244 A | 12/2000 | Suddaby | |
| 6,183,517 B1 | 2/2001 | Suddaby | |
| 6,190,414 B1 | 2/2001 | Young et al. | |
| 6,332,895 B1 * | 12/2001 | Suddaby ................. | 623/17.11 |
| 6,402,785 B1 | 6/2002 | Zdeblick | |
| 6,447,547 B1 | 9/2002 | Michelson | |
| 6,478,823 B1 | 11/2002 | Michelson | |
| 6,500,205 B1 | 12/2002 | Michelson | |
| 6,562,074 B2 | 5/2003 | Gerbec | |
| 6,582,431 B1 | 6/2003 | Ray | |
| 6,648,917 B2 | 11/2003 | Gerbec | |
| 6,652,584 B2 | 11/2003 | Michelson | |
| 6,709,458 B2 | 3/2004 | Michelson | |
| 6,716,247 B2 | 4/2004 | Michelson | |
| 6,793,679 B2 | 9/2004 | Michelson | |
| 6,808,537 B2 | 10/2004 | Michelson | |
| 6,881,228 B2 | 4/2005 | Zdeblick | |
| 6,972,035 B2 | 12/2005 | Michelson | |
| 2002/0156480 A1 | 10/2002 | Overes | |
| 2003/0004575 A1 | 1/2003 | Erickson | |
| 2004/0030387 A1 * | 2/2004 | Landry et al. ............. | 623/16.11 |
| 2004/0088055 A1 | 5/2004 | Hanson et al. | |
| 2005/0113842 A1 | 5/2005 | Bertagnoli et al. | |
| 2006/0241643 A1 * | 10/2006 | Lim et al. ................... | 606/90 |

* cited by examiner

*Primary Examiner*—Thomas C Barrett
*Assistant Examiner*—Nicholas Woodall
(74) *Attorney, Agent, or Firm*—Holland & Hart LLP

(57) ABSTRACT

An expandable spinal fusion device is provided. The expandable device comprises a first part slidingly coupled to a second part. An removable expandable member extends between the first part and the second part and is coupled to a rotating operator such that rotating the operator causes the first part and the second part to move away from each other and distract vertebral bodies. A spacer or clip is used to lock the first part in relation to the second part to allow bone growth the fuse the vertebral bodies.

18 Claims, 4 Drawing Sheets

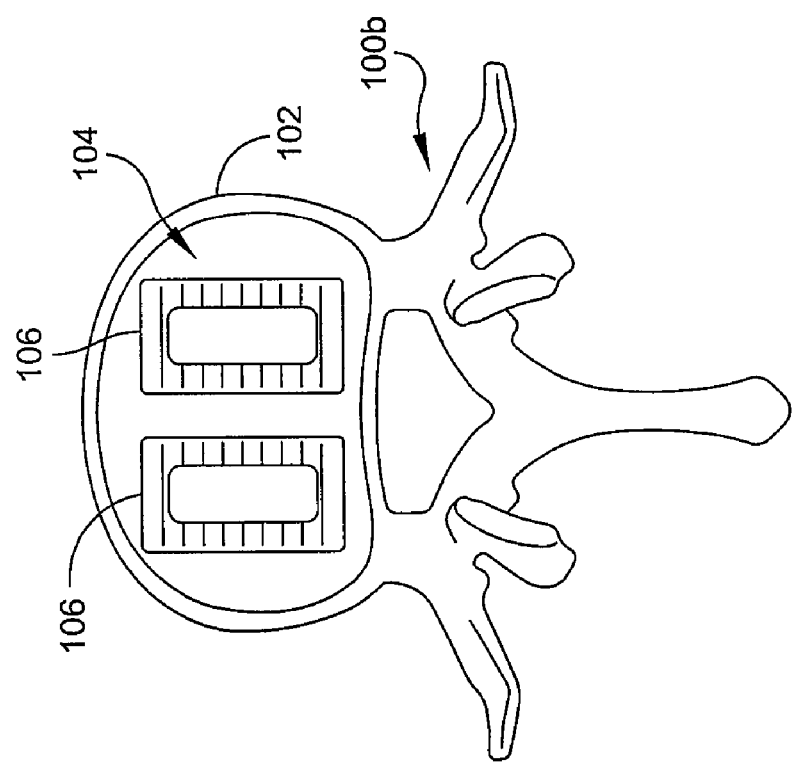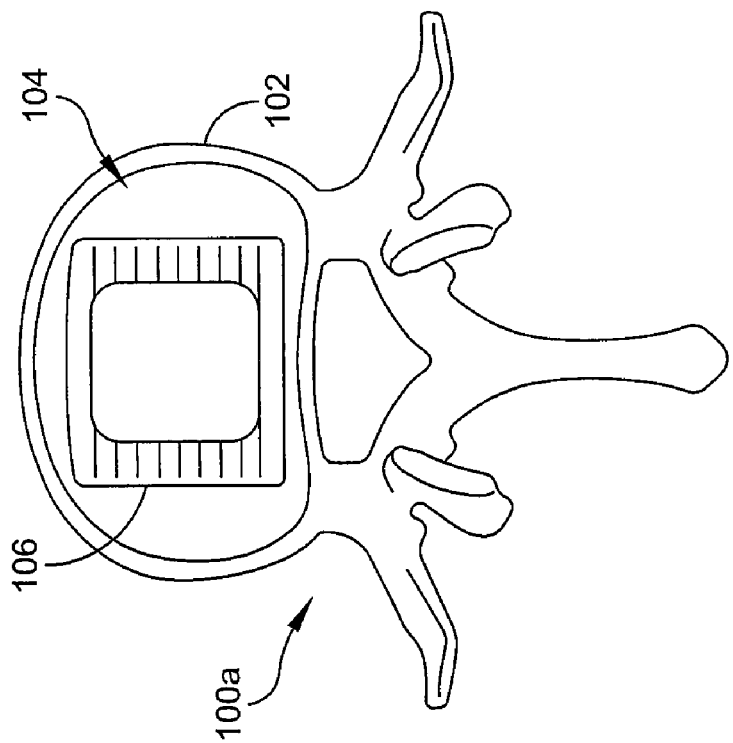
FIG. 1

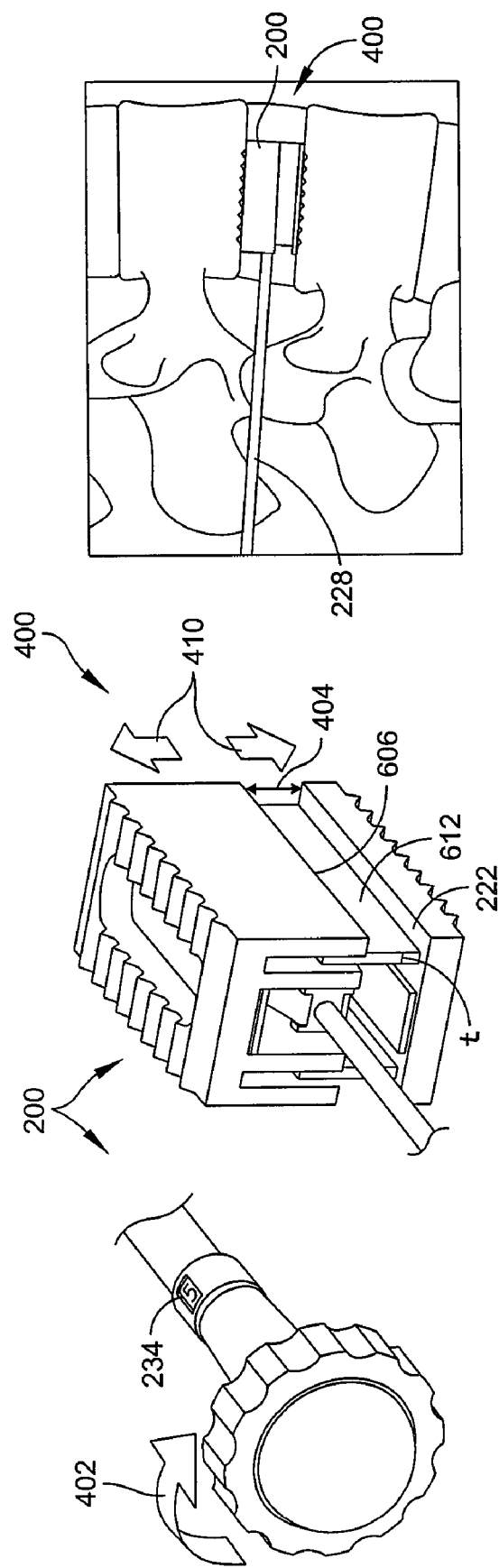

EXPANDABLE SPINAL FUSION CAGE

RELATED APPLICATIONS AND CLAIM OF PRIORITY

The present invention relates to U.S. Provisional Patent Application Ser. No. 60/456,590, filed Mar. 21, 2003, titled Expandable Spinal Fusion Device, which application is expired, the disclosure of which is incorporated herein by reference as if set out in full.

FIELD OF THE INVENTION

The present invention relates to spinal corrective surgery and, more particularly to an expandable spinal fusion cage to facilitate fusing a spinal segment into a solid bone mass.

BACKGROUND OF THE INVENTION

The vertebrae of the human spine are arranged in a column with one vertebra on top of the next. Between each vertebra exists an intervertebral disc that transmits force between adjacent vertebrae and provides a cushion between the adjacent vertebrae.

Sometimes, back pain is caused by degeneration or other deformity of the intervertebral disc ("diseased disc"). Conventionally, surgeons treat diseased discs by surgically removing the diseased disc and inserting an implant in the space vacated by the diseased disc, which implant may be bone or other biocompatible implants. The adjacent vertebrae are then immobilized relative to one another. Eventually, the adjacent vertebrae grow into one solid piece of bone.

For example, a conventional method to fuse vertebrae together includes a bone graft and a plate to stabilize the device. The current process includes inserting a bone graft and fusing the adjacent vertebrae together. Traditionally, inserting a bone graft involves distracting the disc space and manually keeping the vertebral bodies separated. The bone graft or implant is located and, once the implant is placed, the surgeon releases the adjacent vertebrae allowing them to squeeze the implant and hold it in place.

To immobilize the vertebrae with the implant in place, the surgeon next applies a plate over the adjacent vertebrae. The plate may have a central viewing window and one or more screw holes. Typically, four bone screws would be screwed into the vertebrae using the screw holes to anchor the cervical plate to the vertebrae and immobilize the vertebrae with respect to one another.

Immobilizing the superior and inferior vertebrae with a bone graft in the intervertebral disc space prompts fusion of the superior and inferior vertebrae into one solid bone. As can be appreciated, the superior and inferior vertebrae are distracted to allow sufficient space for the surgeon to implant and orient the implant. This tends to increase the trauma to the surrounding tissue. Thus, it would be desirous to develop a compact fusion device that is expandable such that it can be inserted in a compact package allowing surgical site to be smaller, reducing the trauma to surrounding tissue.

SUMMARY OF THE INVENTION

The present invention provides an expandable spinal fusion cage. The expandable spinal fusion cage includes a first part slidably connected to a second part. The first part includes a first vertebral body interface surface and a second surface opposite the first vertebral body interface surface. The second part includes a third vertebral body interface surface and a fourth surface opposite the third vertebral body interface surface. Dual walls coupled to the second surface extend from the second surface towards the fourth surface forming channels. Single walls coupled to the fourth surface extend from the fourth surface towards the second surface. The single walls are aligned the channels. A removable, expandable member extending from the second surface to the fourth surface, the removable, expandable member having a collapsed state and at least one expanded state. An operating arm having a proximate end coupled to the removable, expandable member and a distal end coupled to a rotating operator allows expansion of the removable, expandable member, which slidably moves the first part in relation to the second part. Spacers frictionally fit about the single walls. Such that rotating the rotating operator causes the operating arm to move the removable, expandable member from the collapsed state to the at least one expanded state and the at least one spacer locks the removable, expandable member in the at least one expanded state.

The foregoing and other features, utilities and advantages of the invention will be apparent from the following more particular description of a preferred embodiment of the invention as illustrated in the accompanying drawings.

BRIEF DESCRIPTION OF THE DRAWINGS

The accompanying drawings, which are incorporated in and constitute a part of this specification, illustrate embodiments of the present invention, and together with the description, serve to explain the principles thereof. Like items in the drawings are referred to using the same numerical reference.

FIG. 1 is an axial view of an intervertebral disc space with implants constructed in accordance with an embodiment of the present invention;

FIGS. 4A and 4B show the implant of FIGS. 2A and 2B in an expanded state;

FIG. 5 is a lateral view of the implant of FIGS. 4A and 4B in the intervertebral disc space in an expanded state;

DETAILED DESCRIPTION

Figures 2A, 2B, 3:
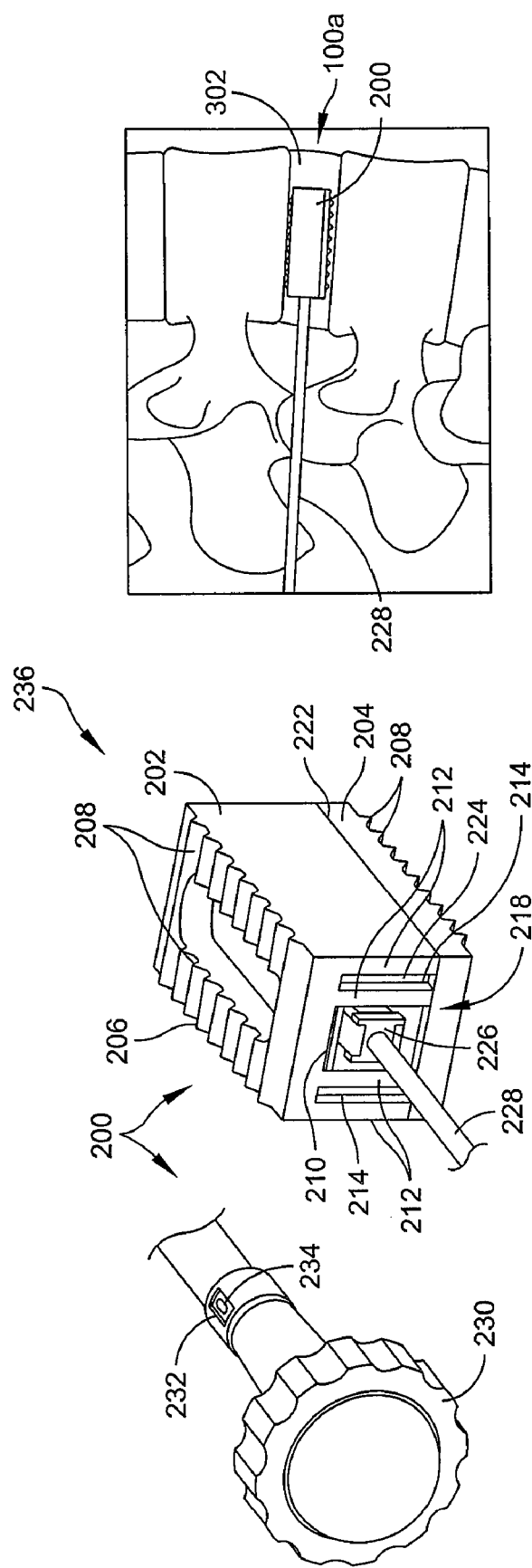
FIGS. 2A and 2B are front partially exploded perspective view of an implant constructed in accordance with an embodiment of the present invention.
FIG. 3 is a lateral view of the implant of FIGS. 2A and 2B in an intervertebral disc space in a collapsed or compact state.
Figure 8:
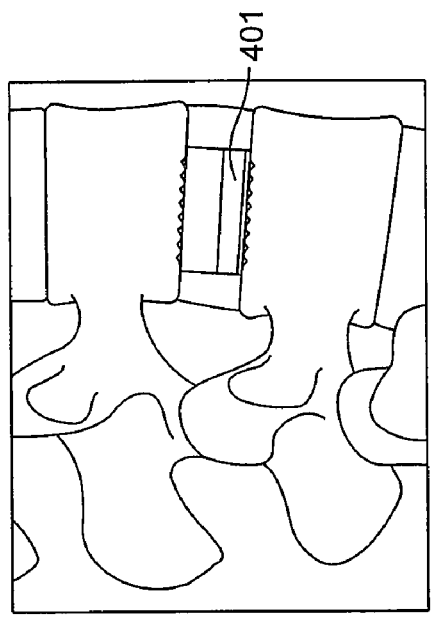
FIG. 8 is a lateral view of the implant of FIG. 7.

The present invention will now be described with reference to the figures. Referring first to FIG. 1, an axial view of spinal segments 100a and 100b is shown. Spinal segment includes inferior vertebral body 102, superior vertebral body (not specifically shown, but substantially identical to inferior vertebral body 102), and intervertebral disc space 104. Intervertebral disc space 104 is typically occupied by an intervertebral disc comprising a disc annulus and disc nucleus. To fuse inferior vertebral body 102 and the superior vertebral body, the intervertebral disc may be fully or partially removed, but is shown as fully removed for convenience. Occupying intervertebral disc space 104 is at least one expandable spinal fusion device 106. Depending on the surgical procedure, such as an anterior or posterior approach, and the discs begin fused, one or more devices 106 may be used by the surgeon. As shown in segment 100a, a single device 106 is used. Spinal segment 100b uses two devices 106.

Referring now to FIGS. 2A and 2B, an expandable fusion device 200 is shown in more detail. Device 200 includes a first part 202 and a second part 204. First part 202 includes a first vertebral body interface surface 206. First vertebral body interface surface 206 may include surface texturing 208, such as the saw tooth projections shown or alternatively, striations, other shaped protrusions, or the like. First part 202 has a second surface 210 opposite first vertebral body interface surface 206. Extending opposite optional surface texturing 208 from second surface 210 are a plurality of dual walls 212. As shown, two sets of dual walls 212 form two channels 214. Dual walls 212 and second surface 216 form a partially enclosed space 218.

Second part 204 comprises a third vertebral body interface surface 220. Second vertebral body interface surface 220 may comprise optional surface texturing 208. Second part 204 also comprises a fourth surface 222 opposite third vertebral body interface surface 220. Extending from fourth surface 222 exist a plurality of single walls 224. Single walls 224 are aligned to slidably engage channels 214. Note, while two dual walls 212 forming two channels are shown on first part 202 and two single walls 224 to align with channels 214 are shown in second part 204, dual walls 212 and single walls 224 may be alternatively arranged on second part and first part respectively. Alternatively, first part may have two dual walls 212 forming one channel 214 and one single wall 224 while second part may have two dual walls 212 forming one channel 214 and one single wall 224 such that the single walls align with the channels.

Residing in space 218 is a removable, expandable member 226. Expandable member 226 operates in any conventional manner, similar to, for example, a car jack. Because the operation of expandable member is well known in the art, it will not be further explained herein. Extending from expandable member 226 is an operating arm 228. Operating arm 228 is connected at a proximate end to expandable member 226 and at a distal end to a rotating operator 230, which is shown as a dial, but could be other rotating devices. Rotating operator 230 has an indicating window 232 and indicia 234 in indicating window 232 to provide information to the surgeon as will be explained further below. As shown in FIGS. 2A and 2B, device 200 is in the collapsed or compact state 236. Correspondingly, indicia 234 indicates "0" or the like to show no expansion or full collapsed state.

Referring now to FIG. 3, spinal segment 100a is shown in a lateral view. Device 200 is implanted in intervertebral disc space 302 initially in the collapsed state 236 with operating arm 228 extending from the disc space 302 to terminate in a position where rotating operator 230 is accessible by a surgeon.

Referring now to FIGS. 4A and 4B, device 200 is shown in an expanded state 400. To obtain expanded state 400, rotating operator 230 is rotated, for example in a clockwise direction as shown by arrow 402. Device 200 may be expandable to a plurality of positions over a spectrum. As device 200 expands to various positions, indicia 234 will indicate the corresponding expansion state in indicating window 232. For example, indicia 234 indicates a position "5" in FIGS. 4A and 4B. Position 5 would correspond to a desired distraction by the surgeon. As rotating operator 230 is rotated, single walls 224 slidably move in channels 214 as shown by arrows 410 such that channels 214 and single walls 224 provide a traveling guide. As single walls 224 moves in channels 214, gaps 404 form between a bottom edge 606 of dual walls 212 and fourth surface 222.

Referring to FIG. 5, device 200 in an expanded state 400 is shown in intervertebral disc space 302. Device 200 provides distraction between superior and inferior vertebral discs.

Figure 7:
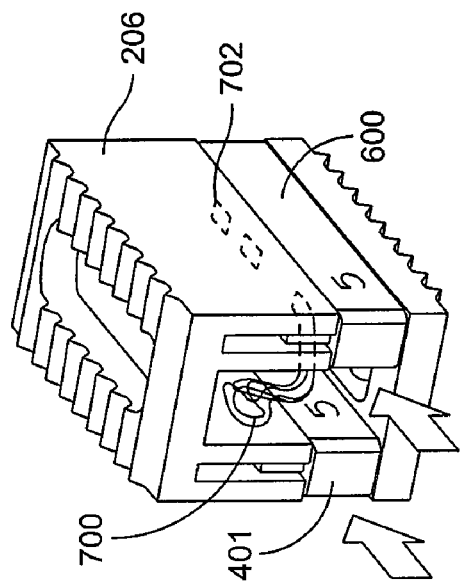
FIG. 7 is a front, perspective view of the implant of FIGS. 4A and 4B with the spacer.
Figure 6:
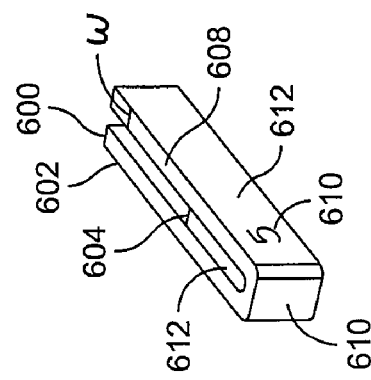
FIG. 6 is a front, perspective view of a spacer constructed in accordance with an embodiment of the present invention.

Referring to FIG. 6, a spacer 600 is shown. Spacer 600 has a plurality of spacer walls 602 separated by a distance 604, which generally corresponds to a thickness t of single wall 224. Spacer walls 602 have a width w of sufficient size such that a bottom edge 606 of dual walls 212 can rest a leading edge 608 of spacer walls 602. Spacer walls extend all or part of the length of single wall 224. A spacer wall connector 610 traverses one end of spacer 600 connecting the spacer walls 602. Spacer 600 forms a frictional fitting with single wall 224. Spacer walls 602 may be parallel as shown, converge, or diverge to facilitate use as a matter of design choice. Single wall 224 and spacer walls 602 may have texturing 612 to facilitate the frictional fitting between spacer 600 and single wall 224. Spacer 600 is sized to fit into gap 404, which corresponds to the expansion state selected by the surgeon. Thus, expansion state corresponding to indicia "1" would have a corresponding spacer 600 as would expansion corresponding to indicia "2", "3", "4", or the like. Thus, spacer 600 has indicia 610 corresponding to indicia 234. Implanting spacer 600 locks device 200 in the expansion selected by the surgeon. In this case, as shown in FIGS. 4A and 4B, spacer 600 corresponding to expansion state 5 as shown by indicia 234 is selected. Referring to FIG. 7, device 200 with spacer 600 is shown.

Once spacers 600 are placed, the surgeon may operate rotating operator 230 back to the collapsed stated, position "0". Once in the collapsed position, expandable member 226 may be removed from space 218. Space 218 may be packed with material 700, such as bone chips or the like, to facilitate bone growth between superior and inferior vertebral discs. Moreover, as shown in phantom in FIG. 7, dual walls 212 and single walls 224 may have channels 702, such as, divots, in growth channels, or the like, to further facilitate bone growth and fusion. Alternatively to removing expandable member, material 700 may be packed about expandable member 226 and operating arm 228 may be detachable and removable from expandable member 226.

First part and second part may be constructed from, for example, a number of biocompatible materials, such as, for example, milled bone, PEEK material, titanium, resorbable material, shaped memory alloys, or the like. First part and second part need not be constructed from the same material.

While the invention has been particularly shown and described with reference to embodiments thereof, it will be understood by those skilled in the art that various other changes in the form and details may be made without departing from the spirit and scope of the invention.

The invention claimed is:

1. An expandable fusion device for use in fusing a vertebral segment, comprising:
  a first part;
  a second part slidably connected to the first part;
  the first part comprising a first vertebral body interface surface and a second surface opposite the first vertebral body interface surface;
  the second part comprising a third vertebral body interface surface and a fourth surface opposite the third vertebral body interface surface;
  at least one dual wall coupled to the second surface and extending from the second surface towards the fourth surface, the at least one dual wall forming at least one channel;
  at least one single wall coupled to the fourth surface and extending from the fourth surface towards the second surface, the at least one single wall aligned with the at least one channel and the at least one single wall and the at least one channel forming a traveling guide with the at least one single wall and the at least one dual wall slidably engaged with one another when the first vertebral body interface surface and the third vertebral body interface surface travel away from one another;

a removable, expandable member extending from the second surface to the fourth surface, the removable, expandable member having a collapsed state and at least one expanded state;

an operating arm having a proximate end coupled to the removable, expandable member and a distal end coupled to a rotating operator, and at least one spacer to form a friction fit with the at least one single wall, wherein rotating the rotating operator causes the operating arm to move the removable, expandable member from the collapsed state to the at least one expanded state and the at least one spacer locks the first part and the second part in the at least one expanded state.

2. The device according to claim 1, wherein the at least one dual wall comprises at least two dual walls and the at least one single wall comprises at least two single walls, and wherein the at least two dual walls and the second surface form a space, the removable, expandable member resides in the space.

3. The device according to claim 2, wherein one of the at least two dual walls is coupled to the fourth surface and one of the at least two single walls is coupled to the second surface.

4. The device according to claim 2, wherein when the device is in the at least one expanded state, material to facilitate bone growth is packed in the space.

5. The device according to claim 1, wherein at least one of the first vertebral body interface surface and the third vertebral body interface surface comprises surface texture.

6. The device according to claim 5, wherein the surface texture comprises at least one of protrusions or striations.

7. The device according to claim 1, wherein the at least one expanded state comprises a plurality of expanded states and further comprising a indicating window and indicia such that rotating the rotating operator causes the device to expand to successively through the plurality of expanded states and the indicia corresponding to the plurality of expanded states indicates in the indicating window.

8. The device according to claim 7, wherein the at least one spacer comprises a plurality of spacers such that the plurality of spacers correspond to the plurality of expanded states and the spacer used to lock the device corresponds to the indicia in the indicating window.

9. The device according to claim 1, further comprising channels in the at least one dual wall and the at least one single wall to facilitate bone growth.

10. The device according to claim 1 made from at least one of milled bone, biocompatible metal, shaped memory alloy, biocompatible plastics, resorbable material, and PEEK material.

11. The device according to claim 1, wherein the operating arm is removably attached to the removable, expandable member.

12. An expandable fusion device for use in fusing a vertebral segment, comprising:

a first part;

a second part slidably connected to the first part;

the first part comprising a first vertebral body interface surface and a second surface opposite the first vertebral body interface surface;

the second part comprising a third vertebral body interface surface and a fourth surface opposite the third vertebral body interface surface;

a plurality of dual walls coupled to the second surface and extending from the second surface towards the fourth surface, each of the dual walls forming a channel;

a plurality of single walls corresponding to the plurality of dual walls, each single wall coupled to the fourth surface and extending from the fourth surface towards the second surface, each of the single walls aligned in sliding relation with a corresponding channel forming a traveling guide with the plurality of single walls and the plurality of dual walls slidably engaged with one another when the first vertebral body interface surface and the third vertebral body interface surface travel away from one another;

the plurality of dual walls and the second surface defining a recess;

a removable, expandable member residing in the recess and extending from the second surface to the fourth surface, the removable, expandable member having a collapsed state and a plurality of predetermined expanded states;

an operating arm having a proximate end coupled to the removable, expandable member and a distal end coupled to a rotating operator, and a plurality of spacers with at least one of the plurality of spacers corresponding to each of the plurality of predetermined expanded states, each spacer to form a friction fit with the plurality of single walls, wherein rotating the rotating operator causes the operating arm to move the removable, expandable member from the collapsed state to the at least one expanded state and the at least one spacer locks the first part and the second part in the at least one expanded state.

13. The device according to claim 12, wherein at least one of the first vertebral body interface surface and the third vertebral body interface surface comprises surface texture to facilitate fusion to the corresponding vertebral body endplate.

14. The device according to claim 12, wherein the rotating operator further comprises an indicating window to display a plurality of indicia, wherein the indicia correspond to the plurality of predetermined expanded states.

15. An expandable fusion device comprising:

a first part having a first vertebral body contacting surface and a first side wall extending away from the first vertebral body contacting surface;

a second part having a second vertebral body contacting surface and a second side wall extending away from the second vertebral body contacting surface, the first and second sidewalls overlapping in sliding arrangement forming a traveling guide with the first and second sidewalls slidably engaged with one another when the first vertebral body contacting surface and the second vertebral body contacting surface interface surface travel away from one another such that the spacing between the first vertebral body contacting surface and second vertebral body contacting surface is adjustable; and a spacer engageable with at least one of the sidewalls to fix a minimum spacing between the first vertebral body contacting surface and second vertebral body contacting surface.

16. The device according to claim 15, wherein the spacer is engageable with at least one of the first sidewall and the second sidewall, the spacer having a height sized to fit into a gap between the first part and the second part, the spacer, when engaged to the at least first or second sidewall, abutting a portion of each of the first and second parts.

17. The device according to claim 16, wherein the spacer is one of a plurality of alternative spacers having different heights.

18. The device according to claim 16, wherein the first side wall comprises a pair of spaced apart sidewalls defining a channel, the second side wall is sized to slide within the channel, and the spacer comprises first and second legs with a separation distance configured to straddle the second side wall.

* * * * *